United States Patent
Ying et al.

(10) Patent No.: US 9,249,433 B2
(45) Date of Patent: Feb. 2, 2016

(54) CLOSTRIDIUM ACETOBUTYLICUM AND APPLICATION THEREOF

(75) Inventors: Hanjie Ying, Nanjing (CN); Dong Liu, Nanjing (CN); Yong Chen, Nanjing (CN); An Li, Nanjing (CN); Tao Zhou, Nanjing (CN); Jinglan Wu, Nanjing (CN); Xiaoqing Lin, Nanjing (CN); Xiaochun Chen, Nanjing (CN); Jingjing Xie, Nanjing (CN); Jianxin Bai, Nanjing (CN)

(73) Assignee: Nanjing University of Technology, Jiangsu (CN)

( * ) Notice: Subject to any disclaimer, the term of this patent is extended or adjusted under 35 U.S.C. 154(b) by 0 days.

(21) Appl. No.: 14/386,286

(22) PCT Filed: Mar. 20, 2012

(86) PCT No.: PCT/CN2012/072649
§ 371 (c)(1),
(2), (4) Date: Nov. 11, 2014

(87) PCT Pub. No.: WO2013/138998
PCT Pub. Date: Sep. 26, 2013

(65) Prior Publication Data
US 2015/0093796 A1    Apr. 2, 2015

(51) Int. Cl.
*C12P 7/26* (2006.01)
*C12R 1/145* (2006.01)
*C12N 1/20* (2006.01)
*C12P 7/16* (2006.01)

(52) U.S. Cl.
CPC ... *C12P 7/26* (2013.01); *C12N 1/20* (2013.01); *C12P 7/16* (2013.01); *C12R 1/145* (2013.01); *Y02E 50/10* (2013.01)

(58) Field of Classification Search
None
See application file for complete search history.

(56) References Cited

PUBLICATIONS

Bahl et al. "Continuous Production of Acetone and Butanol by Clostridium acetobutylicum in a Two-Stage Phosphate Limited Chemostat" European J Appl Microbiol Biotechnol (1982) 15:201-205.*
Evans et al. "Enhancement of Butanol Formation by Clostridium acetobutylicum in the Presence of Decanol-Oleyl Alcohol Mixed Extractants" Applied and Environmental Microbiology, Jul. 1988, p. 1662-1667.*
Lui et al. "Enhanced butanol production by modulation of electron flow in Clostridium acetobutylicum B3 immobilized by surface adsorption" Bioresource Technology 129 (2013) 321-328.*

* cited by examiner

*Primary Examiner* — Thane Underdahl
(74) *Attorney, Agent, or Firm* — Christie, Parker & Hale, LLP

(57) ABSTRACT

The present invention provides *Clostridium acetobutylicum* and an application thereof. A preservation number of the *Clostridium acetobutylicum* provided in the invention is CGMCC No. 5234. The *Clostridium acetobutylicum* provided in the present invention can be used for cogeneration of acetone, butanol, ethanol, and 3-hydroxy butanone through fermentation, so as to improve the economic benefit of butanol fermentation. NAD+ coupling and regeneration can be implemented by adding metabolism or growth regulating substances, so as to improve the product yield, and at the same time, the yield of cogeneration products can be flexibly adjusted, so as to cater for the market demand.

21 Claims, 1 Drawing Sheet

CLOSTRIDIUM ACETOBUTYLICUM AND APPLICATION THEREOF

CROSS-REFERENCE TO RELATED APPLICATION(S)

This application is a National Phase Patent Application and claims priority to and benefit of International Application Number PCT/CN2012/072649, filed on Mar. 20, 2012, the entire disclosure of which is incorporated herein by reference.

TECHNICAL FIELD

The present invention belongs to the technical field of microbe, and relates to a *Clostridium acetobutylicum* for producing 3-hydroxy butanone and use thereof.

BACKGROUND TECHNOLOGIES

Acetone, butanol and ethanol, collectively referred to as ABE, are important raw materials in medicine, pesticide, plastic, rubber and light industry, and are also very important chemical solvents. Therefore, the study of ABE has a very important effect on the development of modern industry.

Acetone, also known as dimethylketone, is a colorless transparent liquid and highly volatile. Acetone is not only an important organic solvent but also an important chemical material, which can be used in explosive, plastic, fiber, leather, spray painting and other industries, and can also used for synthesizing ketene, acetic anhydride, iodoform, polydiene rubber, epoxy resin and the like.

Butanol, also known as 1-butanol, is a colorless transparent liquid with strong odor of alcohol. It is slightly soluble in water. The relative density is 0.81 and the boiling point is 117.7° C. It belongs to a second-stage flammable liquid. Butanol, an important organic materials and chemical solvents, is widely used in various kinds of plastic, rubber goods, resins, leather, papermaking and other light industries. Another important role of butanol is acting as a new biofuel with great potential nowadays, which is known as second-generation biofuels. Compared with ethanol, butanol has a higher combustion value, may support cars running more 30% journey, has similar properties to hydrocarbon, no modification is required for automobile cylinder, has low volatility, is non-hydrophilic and free from corrosion, has good high-octane rating and anti-detonating quality. Hence, under the situation that the fossil resources decrease gradually in the world, the research and development of butanol becomes a new hot topic rapidly.

3-hydroxy butanone, also known as acetoin or acetyl methyl carbinol, is usually light yellow liquid or crystal. It is naturally occurring in corn, grape, berries, cheese, meat and many other foods, and widely used as one of the spices. China's national standard GB2760-86 stipulates that it can be used as food-flavors, and the security number in Flavor and Extract Manufacturers Association (FEMA) is 2008. In addition, 3-hydroxy butanone can also serve as an important raw material in chemical synthesis. For example, it can be used for synthesizing a chiral smectic material and a nematic material.

Traditional chemical preparation of 3-hydroxy butanone is mainly chemical process or enzymatic conversion, the raw material is mainly diacetylbutanedione and 2,3-butanediol. In 1998, Martin Studer et al. from the British Witwatersrand University used modified platinum as a catalyst to selectively hydrogenate, thereby reducing diacetyl, the yield is 30%. Slipszenko from Hull University in British also developed platinum as a catalyst to hydrogenate, thereby reducing diacetyl to form 3-hydroxyl butanone, the yield is 85%. However, heterogeneous catalytic hydrogenation reaction is usually carried out under high pressure, so high quality facility is required and the catalyst used is expensive. In 1992, Hummel et al. from the United States obtained diacetyl reductase from lactobacillus or yeast by adopting microorganism culture methods, and then generated 3-hydroxy butanone under conditions of pH5, 70° C. by using the reductase and coenzyme NADH to catalyze diacetyl, the highest yield is up to 100%. RH Blom from the United States Department of Agriculture synthesized diacetyl and 3-hydroxy butanone from 2,3-butanediol by an oxidative dehydrogenation process in 1945. 2,3-butanediol together with air go through Pyrex tube reactor (copper shavings are filled thereinto) after heated under 140° C., the reaction temperature is 315° C., the products are diacetyl (the yield is 33%) and 3-hydroxy butanone (the yield is 25%). A. Hilmi from Poitiers University in France prepares 3-hydroxy-2-butanone by electrochemical oxidation method, the method is carried out in an electrolytic bath, wherein the diaphragm is an ion exchange membrane and the electrodes in reaction are all reversible hydrogen electrodes. Positive electrode is Pt—Pb, and porous Pt/Ir (10%) is as a counter electrode, the electrolyte is $HClO_4$, the solvent is ultra-pure water, the reaction temperature is 40° C., and the battery voltage is 0.8V. Using this electrolytic oxidation method, the products include diacetyl and carbon dioxide besides 3-hydroxy butanone, the yield is 94%. However, there exist the problems of serious environment pollution and product quality as for the chemical method. Furthermore, the raw materials are mainly from non-renewable fossil resources, which limits the development in the long run.

In addition, 3-hydroxy butanone can also be produced by microbial fermentation. In most microorganisms, two molecules of pyruvic acid synthesize one molecule of acetolactate under the action of acetolactate synthetase, and then acetolactate under the action of acetolactate decarboxylase can form 3-hydroxy butanone. Acetolactate can also be naturally oxidative decarboxylated in the presence of oxygen to generate diacetyl, and then the diacetyl is reduced to generate 3-hydroxy butanone. However, 3-hydroxy butanone can be further reduced to generate 2,3-butanediol, the reaction of generating 3-hydroxy butanone by the reduction of diacetyl and the reaction of generating 2,3-butanediol by the reduction of 3-hydroxy butanone can be catalyzed by the same enzyme (2,3-butanediol dehydrogenase). Therefore, in many microorganisms, 3-hydroxy butanone is often as an intermediate product of 2,3-butanediol, accompanied by the generation of diacetyl, which affects the yield and separation. At present, it has been found that many strains can produce 3-hydroxy butanone, for example: *Lactococcus lactis, Lactobacillus casei, Saccharomyces cerevisiae* and other dairy products or wine fermentation strains, but the yield of 3-hydroxy butanone is less than 1 g/L. *Klebsiella pneumonia, Enterobacter aerogenes, Bacillus subtilis* and the like can also be fermented to produce 3-hydroxy butanone, and this methos has a high yield, but these strains are mainly used to produce 2,3-butanediol, 3-hydroxy butanone is only as by-product. Olson and Johnson convert 226 g/L glucose to 14 g/L 3-hydroxy butanone and 97 g/L 2,3-butanediol using *Enterobacter aerogenes*. Cuiqing M A et al. from Shandong University produce chiral 3-hydroxy butanone and 2,3-butanediol by using recombinant *Escherichia coli* which contains 2,3-butanediol dehydrogenase gene and NADH oxidase gene, the concentration of chiral 3-hydroxy butanone reaches 36 g/L. Chinese patent application CN101008019A discloses the application of *Bacillus subtilis* strain in the preparation of 3-hydroxy butanone, wherein glucose is the main material, this method comprises fermenting 50 L *Bacillus subtilis* SFA-H31 (CGMCC 1869) in fermentation tank for 52 h, the conversion rate reaches 48.26%, the fermentation yield of 3-hydroxy butanone reaches 55.67 g/L, and confirms that the strain does not produce the by-products diacetyl and 2,3-butanediol. However, *Bacillus subtilis* et al. generally are aerobic growth and fermentation, and because one glucose will generate two NADH during the process of converting to 3-hydroxy butanone, if it is only used for producing 3-hydroxy butanone, NADH will be wasted. Meanwhile, as 2,3-butanediol and 3-hydroxy butanone are in the upstream and downstream of the same branch, it is hard for conventional cogeneration to individually regulate metabolic flux of them and effectively use NADH.

SUMMARY OF THE INVENTION

The present invention aims at providing a mutagenic *Clostridium acetobutylicum* for coproducing butanol and 3-hydroxy butanone.

The present invention also aims at providing a method for coproducing butanol and 3-hydroxy butanone.

The object of the present invention is realized by the following technical solution. In one aspect, the present invention provides a *Clostridium acetobutylicum* for coproducing butanol and 3-hydroxy butanone by fermentation, the accession number of the deposit is CGMCC NO. 5234, and the strain had been deposited in the Center for General Microorganism of the Administration Committee of the China Microbiological Culture Collection (referred to as CGMCC) on 9 Sep. 2011, the address of the depositary institution is NO. 1 Beichen West Road, Chaoyang District, Beijing, Institute of Microbiology Chinese Academy of Sciences.

The present invention also provides a use of *Clostridium acetobutylicum* in the coproduction of butanol and 3-hydroxy butanon by fermentation.

In another aspect, the present invention provides a method for coproducing butanol and 3-hydroxy butanone by fermentation, comprising fermenting *Clostridium acetobutylicum* in a liquid fermentation culture medium to produce butanol and 3-hydroxy butanone.

The method of the present invention comprises the following steps: 1) culturing *Clostridium acetobutylicum* in a solid plate medium for 12-36 hours; 2) inoculating the cultured *Clostridium acetobutylicum* in step 1 into a seed culture medium and culturing at 5-39° C. for 10-20 hours; 3) inoculating the cultured *Clostridium acetobutylicum* in step 2 with inoculation quantity of 5%-15% into a liquid fermentation medium and culturing under static conditions at 24-40° C. for 40-85 hours.

Preferably, the liquid fermentation medium contains carbon source, nitrogen source and/or inorganic salts.

Preferably, the carbon source is selected from one or more of glucose, glycerol, corn fructose, starch and xylose with a concentration of 20 g/L-80 g/L.

Preferably, the nitrogen source is selected from one or more of ammonium sulfate, ammonium acetate, corn steep liquor, yeast, yeast extract and urea with a concentration of 0.1 g/L-10 g/L.

Preferably, the inorganic salt is selected from one or more of sodium salts, potassium salts, iron salts, ferrous salts, manganese salts, phosphates and sulfates with a concentration of 0.001 g/L-5 g/L.

Preferably, the liquid fermentation medium further contains trace elements.

Preferably, the trace element is selected from one or more of vitamin B1 (thiamine or hydrochloride thereof), vitamin H (Biotin, vitamin B7) and vitamin $B_x$ (para aminobenzoic acid, vitamin H1).

Preferably, the liquid fermentation medium further contains one or more of metabolic or growth regulators.

Preferably, the metabolic or growth regulator is selected from one or more of acetate, branched chain amino acids and glycerol.

More preferably, the acetate contains one or more of sodium acetate, ammonium acetate, magnesium acetate, calcium acetate and potassium acetate, the concentration is 0.5 g/L-8 g/L after being added to the medium, the time to add the acetate is 0-50 hours after the beginning of fermentation. Extra acetate can be used as the raw material for the synthesis of acetone, which will directly improve the production of acetone. Thus, the acetone generated from sugars reduces, while 3-hydroxy butanone increases under the requirement of regenerating $NAD^+$. Moreover, the addition of acetate can also accelerate the consumption rate of sugar and shorten the fermentation cycle. If acetate is added in early stage of growth, the thallus growth will be inhibited, but the yield of butanol will be increased.

More preferably, the branched chain amino acid comprises one or more of leucine, isoleucine and valine, the concentration is 0.05 g/L-5 g/L after being added to the medium, the time to add the branched-chain amino acids is 0-20 hours after the beginning of fermentation. The branched chain amino acids and 3-hydroxy butanone share the same precursor acetolactate. The present invention can feedback inhibit the synthesis of acetolactate by adding branched chain amino acids, thereby reducing the production of 3-hydroxy butanone and further improving the production of butanol. However, the addition of branched chain amino acids has a certain inhibition effect on thallus growth.

More preferably, the concentration of glycerin is 2 g/L-20 g/L after being added to the medium, the time to add the glycerin is 0-60 hours after the beginning of fermentation. The reduction degree of glycerol is higher than that of glucose, and the metabolism of glycerol can provide more NADH. The present invention can provide NADH for thallus in the reuse of acetic acid and butyric acid at later period by adding glycerol in the fermentation, thus increasing the yield of butanol.

Preferably, the liquid fermentation medium further contains a carrier medium, which can adsorb butyric acid or butanol or is beneficial to the growth of thallus, the medium comprises one or more of activated carbon, fibers, resins, emulsifiers. Butyric acid and butanol are the main inhibitor in the growth of thallus, butyric acid limits the concentration of thallus at an earlier stage, butanol limits the rate and production of thallus at a later stage. The present invention can strengthen the growth of thallus, relieve the inhibition effect from products, enhance the resilience of thallus, and greatly improve the fermentation rate, reduce the cycle and significantly increase the yield of 3-hydroxy-butanone by adding the resins or adsorptive carriers during the fermentation process.

Preferably, the culture is a two-stage culture.

Preferably, the two-stage culture comprises the fermentation temperature, pH or the concentration of fermentable sugars is controlled in two-stage.

More preferably, the fermentation temperature is controlled as follows: within 0-30 hours after the beginning of fermentation, the temperature is controlled at 24-40° C. and then is controlled at 32-37° C. The growth of *Clostridium acetobutylicum* at an early stage consumes initial sugar and produces a large amount of acetic acid, and then enters an alcohol production phase in which acetone and butanol are produced. The growth and metabolism of thallus in the two stages have different behaviors at different temperatures. The present invention adjusts the growth of thallus, the production of alcohol as well as the metabolism in the early stage and in the late stage by changing temperature, which is beneficial to improve the production of metabolite.

More preferably, the pH is controlled as follows: within 0-30 hours after the beginning of fermentation, pH is controlled at 4-5.5, and pH is not controlled after beginning to produce alcohol. PH is very important in the fermentation of *clostridium acetobutylicum*, which can reflect and affect the dissociation of acetic acid, butyric acid and other organic acids in the fermentation solution, thereby affecting thallus to use acids. In some cases, due to the problem of using acid, the fermentation is likely to be lagged for a long time at acid producing period. Therefore, pH acts as a key factor in the production of thallus during the transition stage from the acid producing period to the alcohol producing period. The present invention can ensure that thallus is successfully and rapidly transferred to the alcohol producing period by controlling pH in a suitable level in the acid producing period.

More preferably, the concentration of fermentable sugars is controlled as follows: the concentration is 30-50 g/L at the beginning of the fermentation, when the concentration drops to 10-30 g/L, carbon source is refilled to maintain the concentration in the medium at 10-30 g/L, and carbon source is stopped refilling when the total concentration reaches 60-90 g/L. The growth of the mutagenic *Clostridium acetobutylicum* is inhibited at higher initial sugar concentration, at the same time thallus exhibits different distribution of carbon and sulfur in different sugar concentration. The present invention controls the sugar concentration during the fermentation period, and at the same time achieves the aims of promoting the growth of thallus and keeping the fermentation of thallus in a better distribution of carbon and sulfur by refilling sugar.

The present invention screens out a *Clostridium acetobutylicum* which can produce butanol and 3-hydroxy butanone with a high yield by ultraviolet mutagenesis of *Clostridium acetobutylicum* B3. The mutagenic *Clostridium acetobutylicum* of the present invention has strong acetolactate synthase and acetolactate decarboxylase activities, meanwhile lacks 2,3-butanediol dehydrogenase and isopropanol dehydrogenase activities. It can produce butanol, acetone, ethanol (ABE) and 3-hydroxy butanone with a high yield, and no by-products such as 2,3-butanediol, isopropanol are obtained. In addition, the mutagenic *Clostridium acetobutylicum* has strong oxygen resistance. As for both the seed culture and the fermentation culture, there is no need to remove the residual air by inputting anaerobic gas, and the seed culture and the fermentation culture can be fermented under static conditions without inputting gas and stirring.

The present invention produces butanol, ethanol, acetone and 3-hydroxy butanone (acetoin) by fermenting such strain, achieves the coupling and regeneration of $NAD^+$ and meanwhile performs a directional adjustment and control on carbon metabolic flow. Specifically, the method of coproducing 3-hydroxy butanone by using the mutagenic *Clostridium acetobutylicum* to ferment ABE in the present invention comprises: the mutagenic *Clostridium acetobutylicum* is inoculated into a seed culture medium after cultured on a solid plate for 12-36 h, and cultured for 10-20 hours at 25-39° C., then inoculated into the culture media comprising carbon sources, nitrogen sources, inorganic salts and trace elements with an inoculation amount of 5%-15%, the metabolism or growth regulators are added thereinto to produce butanol and 3-hydroxy butanone with a fermentation time of 40-85 h by anaerobic fermentation.

As shown in FIG. 1, 30%-40% of sugar are converted to acetic acid, butyric acid and the like in the prophase (acid producing period) of ABE fermentation using *clostridium acetobutylicum*. The acetic acid and butyric acid can be reduced to ethanol and butanol, and the reuse efficiency of acetic acid and butyric acid determines the production efficiency of butanol. In the present invention, the method of producing 3-hydroxy butanone by mutagenesis of strain can provide NADH for the reuse of acetic acid and butyric acid to further generate butanol, thereby achieving the coupling and regeneration of $NAD^+$, improving the utilization rate of sugar and the yield of solvent, and this method does not generate 2,3-butylene glycol, isopropanol and other common by-products. Meanwhile, as ABE and 3-hydroxy butanone are produced in different branches and have different correlation with the growth of thallus. Thus, the addition of small molecule effectors or growth regulators into each branch can realize effectively the distribution of carbon flow in the two pathways and adjust flexibly their production to meet market demands.

In summary, the beneficial effects of the invention comprise the following aspects:

(1) The production strains obtained by mutagenesis have strong oxygen resistance, thereby reducing greatly the oxygen avoiding measures in conventional anaerobic fermentation process. As the fermentation is performed under static conditions, ventilation and stirring are not required and the energy consumption and emission are low.

(2) Because there are no by-products such as 2,3-butanediol, isopropanol, formic acid and lactic acid, the yield of the product is improved and the subsequent separation pressure is reduced.

(3) NADH provided by 3-hydroxy butanone can be used to reduce acetic acid and butyric acid to ethanol and butanol, thereby realizing the coupling and regeneration of $NAD^+$ and improving the yield of carbon.

(4) 3-hydroxyl butanone and ABE are in different metabolic braches, the metabolic flow can be flexibly adjusted and better meet the marketing demands.

DEPOSIT INFORMATION OF BIOLOGICAL MATERIAL

*Clostridium acetobutylicum* B3 has been deposited in the Center for General Microorganism of the Administration Committee of the China Microbiological Culture Collection (referred to as CGMCC) on 9 Sep. 2011, the address of the depositary institution is NO. 1 Beichen West Road, Chaoyang District, Beijing, Institute of Microbiology Chinese Academy of Sciences. The accession number of the deposit is CGMCC No. 5234.

BRIEF DESCRIPTION OF THE DRAWINGS

The embodiment of the present invention will be described in detail hereinafter in conjunction with the accompanying drawings, wherein.

DETAILED DESCRIPTION OF THE PREFERRED EMBOD

Figure 1:
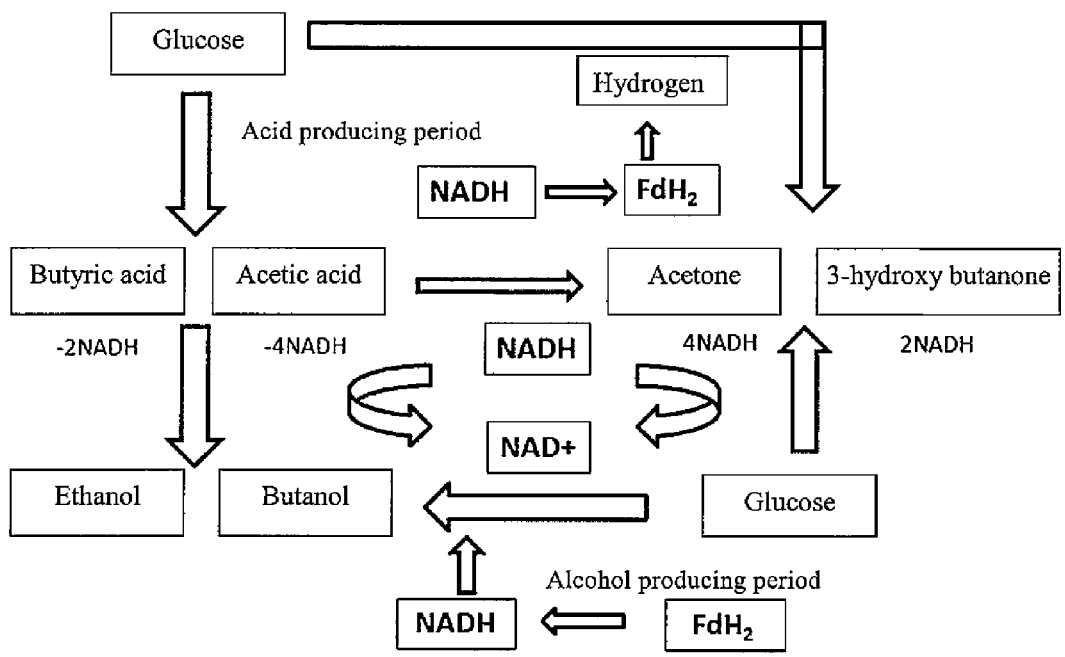
FIG. 1 shows the coproduction of ABE and 3-hydroxy butanone by the coupling and regeneration of $NAD^+$.

The present invention may be better understood according to the following embodiments, however, the ratio of the specific materials, process conditions and results are only intended to illustrate the invention and should not limit the present invention.

The following examples, the medium composition and culture conditions of the plating medium and seed medium are as follows:

Plating medium: glucose 10 g/L, yeast extract 5 g/L, peptone 3 g/L, magnesium sulfate heptahydrate 3 g/L, ammonium acetate 2 g/L, potassium dihydrogen phosphate 1 g/L, dipotassium hydrogen phosphate 1 g/L, agar 15 g/L, sterilized for 15 min at 121° C.

Plate culture conditions: the *Clostridium acetobutylicum* B3 by mutagenesis and screening is streaked on a plate and cultured in Bugbox anaerobic chamber (British Ruskinn) for 24 h at 37° C. White and irregular colonies grew on the plate.

Seed medium: this medium is identical to the above the plating medium, except that agar is not added.

Seed culture conditions: bacterial sludge on the plate is scraped to the seed medium, fermented in 100 mL blue-capped lab bottle or shake flask with a liquid volume of 50%, and cultured under static conditions for 15 h at 37° C., a lot of foam floats on the surface of liquid.

Figure 2:
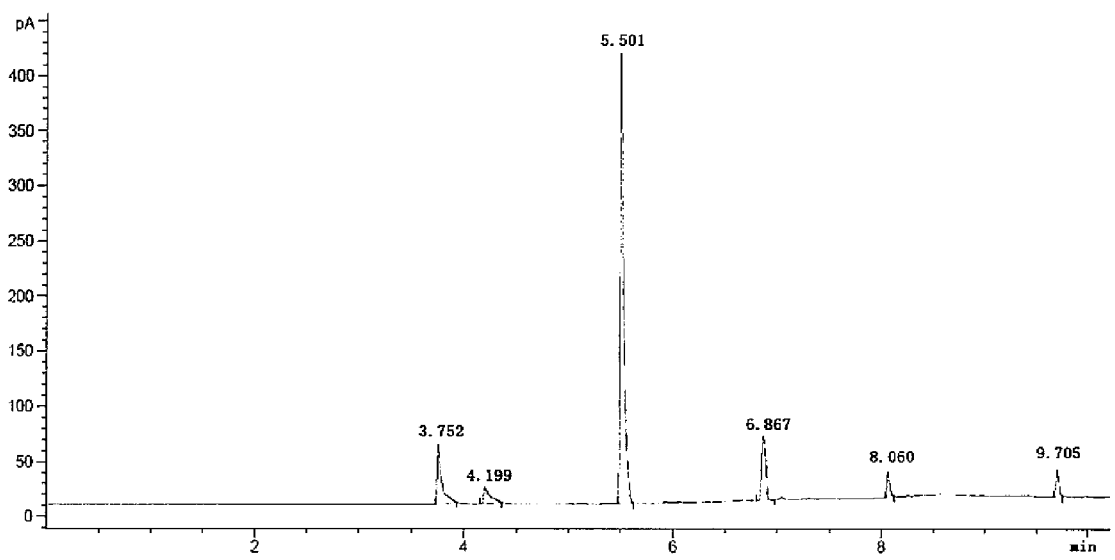
FIG. 2 is the gas chromatogram depending on the samples after fermentation for 30 h in 50 L fermentation tank, the retention time according to the order of peak appearance is as follows: 3.752 min, acetone; 4.199 min, ethanol; 5.501 min., butanol; 6.867 min, 3-hydroxy butanone; 8.060 min, acetic acid; 9.705 min, butyric acid.

The analysis method used in the following examples is gas chromatography (GC), the conditions are as follows: flame ionization detector (FID), Agilent HP-INNO WAX 19091N-236 capillary column (60 m×0.25 mm×0.25 μm), $N_2$ is used as the carrier gas, the flow rate is 2 mL/min, the split ratio is 90:1, the flow rate of $H_2$ is 30 l/min, the flow rate of air is 300 ml/min, the inlet temperature is 180° C., the detector temperature is 220° C., the column temperature (temperature programming): keep 0.5 min at 70° C., then heat up to 190° C. at a rate of 20° C./min and keep 4 min. The representative chromatogram of the detected fermentation products is shown in FIG. 2.

Example 1

Mutagenesis of *Clostridium acetobutylicum*

*Clostridium acetobutylicum* was taken as original strain, activated for 24 h on a plate, and then inoculated once. Bacterial sludge was picked out by an inoculating loop, and placed in a 60 mM sterile aqueous solution of lithium chloride added with 100 glass beads. The volume of the solution was 100 ml. The solution was shaked in a shake flask at a rate of 200 rpm for 10 min to break homogeneously up thallus, then 1 mL of bacterial suspension was taken and placed in a sterile plate for irradiating 90 s in a 254 nm UV irradiation mutagenesis box, diluted 100-fold and coated on a plate containing 20 mg/L of bromcresol purple, cultured under anaerobic conditions at 37° C. for 3 days. Large, fast color-changing colonies having larger and brighter color-changing zone were selected as the primary strains (120 strains in total), fermented after expanding culture, and then the yield and stability were validated. Eventually, a strain of *Clostridium acetobutylicum* B3 was obtained and deposited in the Center for General Microorganism of the Administration Committee of the China Microbiological Culture Collection (referred to as CGMCC) on 9 Sep. 2011, the accession number of the deposit is CGMCC No. 5234. The average yield of butanol from the strain was 11.3 g/L, the average yield of 3-hydroxy butanone was 2.8 g/L, the total amount of solvent was 19.6 g/L and the yield was no less than 10% of the average yield after the strain passaged 8 times. The screened *Clostridium acetobutylicum* B3 had the following physical characteristics:

(1) when cultured in a plate, the colonies were round with a diameter of 4-8 mm, white or gray, had protrusions and irregular edges, and the colonies were thick and easily to provoke.

(2) when cultured in a liquid would, a lot of foam was generated, in addition, there would be flocculent mucosa or filaments, and there was white powdery precipitate at the bottom of bottle or tank after finishing fermentation.

(3) being gram-positive; the cells were long rod-shaped, terminal spore appeared at the later period of fermentation; being anaerobic, but no anaerobic gas was required during the fermentation process, and there was no need to seal the fermentation container.

(4) having a high acetolactate synthase activity, and the activity of the enzyme was easily inhibited by branched chain amino acids.

(5) there were no detectable formic acid, lactic acid, citric acid and glycerol in fermentation samples, but these substances could be used.

Example 2

Fermentation medium: glucose 60 g/L, ammonium acetate 3 g/L, corn steep liquor 2 ml/L, sterilized at 121° C. for 15 min.

The seed liquids were mixed, and then inoculated into a 5 L fermenter with inoculation quantity of 10% and liquid volume of 60%, cultured under static conditions at 37° C. for 80 h.

In the final fermentation liquid, acetone is 3.9 g/L, ethanol is 0.8 g/L, butanol is 11.9 g/L, and 3-hydroxyl butanone is 2.4 g/L.

Example 3

Fermentation medium: 6% of corn flour, pasted for 60 min in the boiling water, sterilized at 121° C. for 30 min.

The seed liquids were mixed, and then inoculated into a 5 L fermenter with inoculation quantity of 5% and liquid volume of 3 L, cultured under static conditions at 37° C. for 50 h.

In the final fermentation liquid, acetone is 4.2 g/L, ethanol is 1.1 g/L, butanol is 11.8 g/L, and 3-hydroxyl butanone is 2.1 g/L.

Example 4

Fermentation medium: glucose 60 g/L, ammonium acetate 2.5 g/L, magnesium sulfate heptahydrate 0.5 g/L, potassium dihydrogen phosphate 0.5 g/L, dipotassium hydrogen phosphate 0.5 g/L, ferrous sulfate heptahydrate 0.01 g/L, sodium chloride 0.01 g/L, sterilized at 121° C. for 30 min.

The seed liquids were inoculated into a 5 L fermenter with inoculation quantity of 10% and liquid volume of 3 L, and then cultured under static conditions at 37° C. for 80 h.

In the final fermentation liquid, acetone is 4.1 g/L, ethanol is 1.1 g/L, butanol is 12.2 g/L, and 3-hydroxyl butanone is 2.3 g/L.

Example 5

The method is the same as Example 4, except that 3 g/L sodium acetate was added when the fermentation lasts 30 h, and the fermentation time was 72 h.

In the final fermentation liquid, acetone is 5.2 g/L, ethanol is 1.1 g/L, butanol is 12.5 g/L, and 3-hydroxyl butanone is 1.9 g/L.

Example 6

The method is the same as Example 4, except that 0.5 g IL valine and 0.5 g IL leucine were added at early stage of fermentation, and the fermentation time was 85 h.

In the final fermentation liquid, acetone is 4.8 g/L, ethanol is 1.1 g/L, butanol is 12 g/L, and 3-hydroxyl butanone is 1.6 g/L.

Example 7

The method is the same as Example 4, except that 5 g/L glycerol was added when the fermentation lasts 40 h, and the fermentation time was 80 h.

In the final fermentation liquid, acetone is 3.9 g/L, ethanol is 1.5 g/L, butanol is 12.8 g/L, and 3-hydroxyl butanone is 2.0 g/L.

Example 8

The method is the same as Example 4, except that resin was added to adsorb butanol when the concentration of butanol reached 5 g/L or so, the resin was added in such an amount that it can adsorb half of the maximum alcohol production, stirring was performed for 5 min every 10 h, and the fermentation time was 65 h.

In the final fermentation liquid, acetone is 3.0 g/L, ethanol is 1.1 g/L, butanol is 11.8 g/L, and 3-hydroxyl butanone is 3.5 g/L.

Example 9

The method is the same as Example 4, except that the temperature was maintained at 38° C. at 0-15 h after fermentation, and then maintained at 34° C., and the fermentation time was 72 h.

In the final fermentation liquid, acetone is 3.1 g/L, ethanol is 1.1 g/L, butanol is 11.4 g/L, and 3-hydroxyl butanone is 2.5 g/L.

Example 10

The method is the same as Example 4, except that the temperature was maintained at 27° C. at 0-35 h after fermentation, and then maintained at 34° C., and the fermentation time was 80 h.

In the final fermentation liquid, acetone is 3.2 g/L, ethanol is 1 g/L, butanol is 11.8 g/L, and 3-hydroxyl butanone is 2.5 g/L.

Example 11

The method is the same as Example 4, except that pH of the medium was controlled at 4.5 by 1M sodium hydroxide solution at 0-30 h after fermentation, and pH was not controlled after the start of alcohol production, and the fermentation time was 80 h.

In the final fermentation liquid, acetone is 3.0 g/L, ethanol is 0.9 g/L, butanol is 11.2 g/L, 3-hydroxyl butanone is 2.5 g/L.

Example 12

The method is the same as Example 4, except that the initial sugar concentration of the medium was 40 g/L, 10 g/L of glucose was supplemented every 10 h when the initial sugar concentration reduced to 15 g/L, supplement was performed 3 times in total, the total sugar concentration reached 70 g/L, and the fermentation time was 80 h.

In the final fermentation liquid, acetone is 5.0 g/L, ethanol 1.4 g/L, butanol 13.8 g/L, and 3-hydroxyl butanone is 3.6 g/L.

REFERENCES

Studer M, Okafor V, Blaser H U, 1998. Hydrogenation of butane-2,3-dione with heterogeneous cinchona modified platinum catalysts: a combination of an enantioselective reaction and kinetic resolution[J]. Chem Commun, 1053~1 054.

Slipszenko J A, Griffiths S P, Simons K E, et al., 1998. Enantioselective hydrogenation[J]. Journal of Catalysts, 179: 267~276.

Hummel W, 1992. Microbiologically prepared diacetyl reductase [P]. U.S. Pat. No. 5,164,314, 1992, 17 Nov.

Blom R H, 1945. Configuration of acetylmethylcarbinol [J]. Am Chem Soc, 67: 494-498.

Hilmi A, Belgsir E M, Leger J M, et al. 1997. Electrocatalytic oxidation of aliphatic diols. Part V. Electro-oxidation of butanediols on platinum based electrodes [J]. Journal of Electroanalytical Chemistry, 435: 69~75.

Olson B H, Johnson M J, 1948. The production of 2,3-butylene glycol by *Aerobacter aerogenes*. J bacterial. 55: 209-222.

Cuiqing M A, Chuanjuan L V, Zijun X I A O, Jiayang Q I N, Ping X U. Gene recombination bacterium and application thereof in preparing chiral pure acetoin and 2,3-butanediol [P], CN101565685A, 2009 Oct. 28.

Jianjun L I U, Xiangying Z H A O, Yanjun T I A N, et al. Use of *Bacillus subtilis* (Ehrenberg) Cohn in preparing 3-hydroxy butanone [P], CN101008019, 2007 Aug. 1.

What is claimed is:

1. A *Clostridium acetobutylicum* for coproducing butanol and 3-hydroxy butanone by fermentation having the deposit accession number CGMCC NO.5234.

2. A method for coproducing butanol and 3-hydroxy butanone by fermentation under static conditions, wherein the method comprises fermenting *Clostridium acetobutylicum* according to claim 1 in a liquid fermentation culture medium to produce butanol and 3-hydroxy butanone.

3. The method according to claim 2, wherein the culture is a two-stage culture.

4. The method according to claim 3, wherein, the two-stage culture comprises a fermentation temperature, a pH or a concentration of fermentable sugars is controlled in two-stage.

5. The method according to claim 4, wherein the fermentation temperature is controlled as follows: within 0-30 hours after the beginning of fermentation, the temperature is controlled at 24-40° C., and then is controlled at 32-37° C.

6. The method according to claim 4, wherein, the pH is controlled as follows: within 0-30 hours after the beginning of fermentation, pH is controlled at 4-5.5, and pH is not controlled after beginning to produce alcohol.

7. The method according to claim 4, wherein, the concentration of fermentable sugars is controlled as follows: the concentration is 30-50 g/L at the beginning of the fermentation, when the concentration drops to 10-30 g/L, carbon source is refilled to maintain the concentration in the medium at 10-30 g/L, and the carbon source is stopped refilling when the total concentration reaches 60-90 g/L.

8. The method according to claim 2, wherein the method comprises the following steps:

1) culturing *Clostridium acetobutylicum* according to claim 1 in a solid plate medium for 12-36 hours;
2) inoculating the cultured *Clostridium acetobutylicum* in step 1 into a seed culture medium, and culturing at 5-39° C. for 10-20 hours; and
3) inoculating the cultured *Clostridium acetobutylicum* in step 2 with inoculation quantity of 5%-15% into a liquid fermentation medium, culturing under static conditions at 24-40° C. for 40-85 hours.

9. The method according to claim 2, wherein the liquid fermentation medium contains carbon source, nitrogen source and/or inorganic salts.

10. The method according to claim 9, wherein, the carbon source is selected from one or more of glucose, glycerol, corn flour, fructose, starch and xylose with a concentration of 20 g/L-80 g/L.

11. The method according to claim 9, wherein, the nitrogen source is selected from one or more of ammonium sulfate, ammonium acetate, corn steep liquor, yeast, yeast extract and urea with a concentration of 0.1 g/L-10 g/L.

12. The method according to claim 9, wherein, the inorganic salt is selected from one or more of sodium salts, potassium salts, iron salts, ferrous salts, manganese salts, phosphates and sulfates with a concentration of 0.001 g/L-5 g/L.

13. The method according to claim 2, wherein the liquid fermentation medium further contains trace elements.

14. The method according to claim 13, wherein, the trace element is selected from one or more of vitamin B1 or hydrochloride thereof, vitamin H and vitamin Bx with a concentration of 0.0001 g/L-3 g/L.

15. The method according to claim 2, wherein the liquid fermentation medium further contains one or more of metabolic or growth regulators.

16. The method according to claim 15, wherein, the metabolic or growth regulator is selected from one or more of acetate, branched chain amino acids and glycerol.

17. The method according to claim 16, wherein, the acetate contains one or more of sodium acetate, ammonium acetate, magnesium acetate, calcium acetate and potassium, the concentration is 0.5 g/L-8 g/L after being added to the medium, and the time to add the acetate is 0-50 hours after the beginning of fermentation.

18. The method according to claim 16, wherein, the branched-chain amino acid comprises one or more of leucine, isoleucine and valine, the concentration is 0.05 g/L-5 g/L after being added to the medium, and the time to add the branched-chain amino acids is 0-20 hours after the beginning of fermentation.

19. The method according to claim 16, wherein, the concentration of glycerol is 2 g/L-20 g/L after being added to the medium, and the time to add the glycerol is 0-60 hours after the beginning of fermentation.

20. The method according to claim 3, wherein the liquid fermentation medium further contains a carrier medium, which can adsorb butyric acid or butanol or is beneficial to the growth of thallus.

21. The method according to claim 20, wherein the carrier medium comprises one or more of resins, activated carbon, fibers, and emulsifiers.

\* \* \* \* \*